United States Patent [19]

Schacht et al.

[11] 4,070,461

[45] Jan. 24, 1978

[54] BIPHENYLYL ETHERS

[75] Inventors: Erich Schacht; Rochus Jonas; Werner Mehrhof; Herbert Nowak; Zdenek Simane; Reinhard Lissner, all of Darmstadt, Germany

[73] Assignee: Merck Patent Gesellschaft mit beschrankter Haftung, Darmstadt, Germany

[21] Appl. No.: 655,545

[22] Filed: Feb. 5, 1976

[30] Foreign Application Priority Data

Feb. 8, 1975 Germany ............................. 2505423

[51] Int. Cl.² .................. A61K 31/435; A61K 31/55; C07D 295/08
[52] U.S. Cl. ............................... 424/232; 260/239 B; 260/326.5 M; 260/293.83; 260/348.11; 260/348.12; 424/248.58; 424/267; 424/274; 424/244
[58] Field of Search .................... 260/239 B, 326.5 M, 260/293.83; 424/244, 267, 274, 232

[56] References Cited

U.S. PATENT DOCUMENTS

| 3,051,709 | 8/1962 | Shapiro et al. | 260/326.5 FM |
| 3,203,992 | 8/1965 | Kanz et al. | 260/326.5 FM |
| 3,337,628 | 8/1967 | Crowther et al. | 260/570.7 |
| 3,501,769 | 3/1970 | Crowther | 260/501.17 |
| 3,534,085 | 10/1970 | Narayanan | 260/239 B |
| 3,652,590 | 3/1972 | Bach | 260/293.83 |
| 3,723,476 | 3/1973 | Nakanishi et al. | 260/293.83 |
| 3,754,003 | 8/1973 | Pedrazzoli et al. | 260/326.5 FM |
| 3,954,776 | 5/1976 | Muro et al. | 260/293.67 |
| 3,984,436 | 10/1976 | Jaeggi et al. | 424/267 |

FOREIGN PATENT DOCUMENTS 1,494,749  9/1967  France ............................. 260/570.7

OTHER PUBLICATIONS

Hoefle et al., Chem. Abs. 82, 106198d, (1975).
Zenno et al., J. Chem. Abs. 82, 155738p, (1974).
Molho II, Chem. Abs. 71, 101530u, (1968).
Zenno et al., II, Chem. Abs. 74, 42142f, (1970).
Kurihara et al., Chem. Abs. 64, 12664a, (1964).
Crowther et al., III, J. Med. Chem. II, 1009–1013, (1968).

*Primary Examiner*—Alton D. Rollins
*Assistant Examiner*—Mark L. Berch
*Attorney, Agent, or Firm*—Millen & White

[57] ABSTRACT

Biphenylyl ethers of the formula

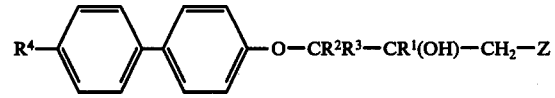

and their physiologically acceptable acid addition salts exhibit pharmaceutically useful serum cholesterol and triglyceride lowering, fibrinolytic, thrombocyte aggregation inhibition, $\beta$-receptor blocking and neuroleptic effects.

15 Claims, No Drawings

BIPHENYLYL ETHERS

BACKGROUND OF THE INVENTION

The invention relates to the new biphenylyl ethers of the general Formula I

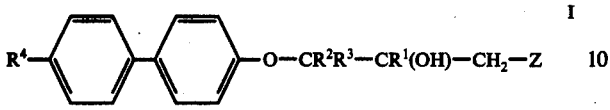

wherein $R^1$, $R^2$ and $R^3$ are each H or $CH_3$; $R^4$ is H, F, Cl, Br or $CF_3$; Z (when $R^2 = R^3 = H$) is piperidino or morpholino each of which is monosubstituted or polysubstituted by alkyl having 1–4 C atoms, and Z (when $R^2 = CH_3$) is morpholino, pyrrolidino, homopiperidino or piperidino which is optionally monosubstituted or polysubstituted by alkyl having 1–4 C atoms or by a hydroxyl group; and to physiologically acceptable acid addition salts thereof.

BRIEF DESCRIPTION OF THE PRIOR ART

Many efforts are being directed nowadays to develop medicaments useful in the treatment of hyperlipoproteinemias and in the prophylaxis and treatment of cardiac and vascular diseases. Clofibrate has been used extensively in the treatment of hyperlipoproteinemias. Nevertheless, it would be advantageous to have available well tolerated compounds which exhibited additional useful activities in conjunction with lowering elevated serum cholesterol and lipoprotein levels, especially activities useful in prophylaxis and treatment of cardiac and vascular diseases. The present invention fills such needs.

Similar compounds are described in our copending application Ser. No. 518,811.

OBJECTS OF THE INVENTION

Accordingly, it is a general object of this invention to provide compounds having pharmaceutically useful serum cholesterol and triglyceride lowering activity.

Another object of this invention is to provide a method and pharmaceutical composition useful in lowering elevated serum cholesterol and triglyceride levels, particularly in animals afflicted with hyperlipoproteinamia, especially in humans.

A further object of this invention is to provide compounds having pharmaceutically useful fibrinolytic, thrombocyte aggregation-inhibiting, β-receptor blocking and neuroleptic effects, especially in conjunction with the aforementioned effects on serum cholesterol and triglyceride levels.

An additional object of this invention is to provide a method and pharmaceutical composition useful in promoting fibrinolysis and in inhibiting thrombocyte aggregation.

Yet another object of this invention is to provide a method and pharmaceutical composition useful in blocking Beta adrenergic receptors which function in vasodilation, cardioacceleration, increased myocardial strength, myometrial relaxation and bronchial relaxation.

Still another object of this invention is to provide a method and pharmaceutical composition useful in neuroleptic stimulation of the sympathetic nervous system in mammals.

Upon study of the specification and appended claims, further objects and advantages of this invention will become apparent to those skilled in the art.

SUMMARY OF THE INVENTION

Briefly, the above and other objects are attained in one aspect of this invention by providing a compound selected from the group consisting of biphenylyl ethers of the formula

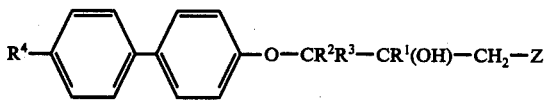

wherein $R^1$, $R^2$ and $R^3$ are each H or $CH_3$; $R^4$ is H, F, Cl, Br or $CF^3$; when $R^2 = R^3 = H$, Z is piperidino or morpholino each of which is monosubstituted or polysubstituted by alkyl of 1–4 C atoms, and when $R^2 = CH_3$, Z is morpholino, pyrrolidino, homopiperidino or piperidino which is optionally monosubstituted or polysubstituted by alkyl of 1–4 C atoms or by hydroxyl; and the physiologically acceptable acid addition salts thereof.

DETAILED DISCUSSION

It has been found that these compounds are well tolerated and possess very valuable pharmacological properties. Above all, effects are found which lower the cholesterol level and lower the triglyceride level and which can be determined in the serum of rats by the methods described by Levine and collaborators in Automation in Analytical Chemistry, Technicon Symposium, 1967, Mediad, New York, pages 25–28, and by Noble and Campbell in Clin. Chem. 16 (1970), pages 166–170.

The compounds also exhibit very good fibrinolytic effects and thrombocyte aggregation-inhibiting effects, besides β-receptor blocking effects and effects on the central nervous system, particularly neuroleptic effects, all of which can also be determined by methods which are currently used for these purposes. The compounds thus display a very broad spectrum of valuable effects.

The compounds can accordingly be employed as medicaments, in particular for the treatment of hyperlipoproteinemias and for the prophylaxis and treatment of cardiac and vascular diseases. They can also be used as intermediate products for the preparation of other medicaments.

In the following text the group p-$R^4$—$C_6H_4$—p—$C_6H_4$ in Formula I is referred to, for brevity, as the radical R. The radical $R^4$ is preferably H but also can be F or Cl as well as Br or $CF_3$. Accordingly, the radical R is preferably an unsubstituted 4-biphenylyl radical, 4'-fluoro-4-biphenylyl, 4'-chloro-4-biphenylyl, 4'-bromo-4-biphenylyl or 4'-trifluoromethyl-4-biphenylyl.

The radical $R^1$ is preferably hydrogen. The radicals $R^2$ and $R^3$ are preferably identical.

Alkyl groups which may be present in the radical Z are preferably methyl groups. Alkyl can, however, also be ethyl, n-propyl, isopropyl, n-butyl, isobutyl, sec.-butyl or tert.-butyl. The radical Z optionally contains up to 10, preferably 1–4 and particularly 1 or 2 such lower alkyl groups.

The radical Z is preferably 2,6-dimethylpiperidino; also, for example, methylpiperidino such as 2-, 3- or 4-methylpiperidino; dimethylpiperidino such as 2,2-, 2,3-, 2,4-, 2,5-, 3,3-, 3,4-, 3,5- or 4,4-dimethylpiperidino;

trimethylpiperidino such as 2,2,3-, 2,2,4-, 2,2,5-, 2,2,6-, 2,3,3-, 2,3,4-, 2,3,5-, 2,3,6-, 2,4,4-, 2,4,5-, 2,4,6- or 2,5,5-trimethylpiperidino; tetramethylpiperidino such as 2,2,6,6- or 3,3,5,5-tetramethylpiperidino; penta-, hexa-, hepta-, octa-, nona- or deca-methylpiperidino; ethylpiperidino such as 2-, 3-or 4-ethylpiperidino; diethylpiperidino such as 2,6-diethylpiperidino; methylethylpiperidino such as 2-methyl-6-ethylpiperidino; and also (when $R^2 = R^3 = H$) 2- or 3-methylmorpholino; 2,2-, 2,3-, 2,5-, 2,6-, 3,3- or 3,5-dimethylmorpholino; 2- or 3-ethylmorpholino; 2,6-diethylmorpholino and the like and (when $R^2$ and/or $R^3$ are $CH_3$) piperidino, pyrrolidino, homopiperidino, morpholino, 3-hydroxypiperidino or 4-hydroxypiperidino.

Accordingly, the invention relates particularly to those compounds of the Formula I in which at least one of the radicals R, $R^1$, $R^2$, $R^3$ and/or Z has one of the preferred meanings indicated in the preceding text.

Some of these preferred groups of compounds can be expressed by the following partial Formulae (a) to (m) which correspond to Formula I and in which the radicals not defined more precisely have the meaning indicated in Formula I, but in which

| | |
|---|---|
| (a) $R^1$ | is H; |
| (b) $R^2$ and $R^3$ | are both H; |
| (c) $R^2$ and $R^3$ | are both $CH_3$; |
| (d) $R^4$ | is H, F or Cl |
| (e) $R^4$ | is H; |
| (f) Z | (when $R^2 = R^3 = H$) is piperidino or morpholino each of which is monosubstituted or polysubstituted by methyl, or (when $R^2 = CH_3$) is morpholino, pyrrolidino, homopiperidino or piperidino which is optionally monosubstituted or polysubstituted by methyl or hydroxyl; |
| (g) Z | is piperidino which is monosubstituted or polysubstituted by methyl; |
| (h) $R^2$ and $R^3$ Z | are both H and is piperidino or morpholino each of which is monosubstituted or polysubstituted by methyl; |
| (i) $R^2$ Z | is $CH_3$ and is morpholino, pyrrolidino, homopiperidino or piperidino which is optionally monosubstituted or polysubstituted by methyl or hydroxyl; |
| (j) $R^1$, $R^2$ and $R^3$ Z | are each H and is piperidino which is monosubstituted to tetrasubstituted by methyl; |
| (k) $R^1$ $R^2$ and $R^3$ Z | is H are both $CH_3$ and is morpholino, pyrrolidino, piperidino, homopiperidino or piperidino which is monosubstituted to tetrasubstituted by methyl; |
| (l) $R^1$, $R^2$ and $R^3$ Z | are each H and is 2-, 3- or 4-methylpiperidino; 2,6- or 3,5-dimethylpiperidino; 2,2,6,6-tetramethylpiperidino; or 2,6-dimethylmorpholino; and |
| (m) $R^1$ $R^2$ and $R^3$ Z | is H, are both $CH_3$ and is morpholino, piperidino, homopiperidino, 4-methylpiperidino or 2,6-dimethylpiperidino. |

A further object of the invention is to provide a process for the preparation of biphenyl ethers of Formula I and of physiologically acceptable acid addition salts thereof, which is characterized in that a. a compound of the general Formula II $$R-O-CR^2R^3-Y \qquad II$$

wherein
R is the radical

Y is

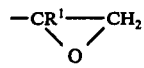

or $-CR^1(OH)-CH_2X$,

X is Hal or a free or functionally modified reactive OH group,

Hal is Cl, Br or I and $R^1$ to $R^4$ have the meanings indicated above is reacted with an amine of the general Formula III $$H-Z \qquad III$$

wherein Z has the meaning indicated above; or b. a phenol of the general Formula IV $$R-OH \qquad IV$$

wherein R has the meaning indicated above is reacted with an amine of the general Formula V $$Y^1-CH_2-Z \qquad V$$

wherein $Y^1$ is

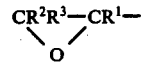

or $X-CR^2R^3-CR^1(OH)-$ and $R^1$, $R^2$, $R^3$, X and Z has the meaning indicated above; or c. an amine of the general Formula VI $$R-O-CR^2R^3-CR^1(OH)-CH_2NH_2 \qquad VI$$

wherein R, $R^1$, $R^2$ and $R^3$ have the meanings indicated above is reacted with a compound of the general Formula VII $$X-W-X \qquad VII$$

wherein W (when $R^2 = R^3 = H$) is pentamethylene or 3-oxapentamethylene each of which is monosubstituted or polysubstituted by alkyl having 1-4 C atoms, or (when $R^2 = CH_3$) is 3-oxapentamethylene, tetramethylene, pentamethylene or hexamethylene which is optionally monosubstituted or polysubstituted by alkyl having 1-4 C atoms or by hydroxyl and X has the meaning indicated above; or d. an aminoketone of the general Formula VIII $$R-O-CR^2R^3-CO-CH_2-Z \qquad VIII$$

wherein R, $R^2$, $R^3$ and Z have the meanings indicated above is reacted with a reducing agent or with a compound of the general Formula IX $$Ch_3-M \qquad IX$$

wherein M is a metal atom or the group -MgHal; or e. a compound of the general Formula X

R—O—CR²R³—CR¹(OH)E      X wherein E corresponds to the group —CH₂—Z, but wherein two hydrogen atoms have been replaced by an oxygen atom and R, R¹, R² and R³ have the meanings indicated above, is treated with a reducing agent, and, if appropriate, a resulting base of Formula I is converted by treatment with an acid into a physiologically acceptable acid addition salt, and/or a resulting acid addition salt is converted by treatment with a base into the free base I.

The preparation of the compounds of Formula I is carried out in other respects by methods which are in themselves known, such as are described in the literature (for example in the standard works such as Houben-Weyl, Methoden der Organischen Chemie (Methods of Organic Chemistry), Georg-Thieme-Verlag, Struttgart; and Organic Reactions, John Wiley & Sons, Inc., New York), under reaction conditions known to be suitable for these reactions. If desired, the starting materials for the preparation of the compounds of Formula I can also be formed in situ.

The radical Y is preferably oxiranyl or 1-methyloxiranyl. The radical X is preferably Cl or Br; it can, however, also be I, OH or a functionally modified OH group. Functionally modified OH groups are understood here, in particular, as reactive, esterified OH groups, for example alkylsulphonyloxy having preferably 1–6 C atoms, e.g. methanesulphonyloxy, or arylsulphonyloxy having preferably 6–10 C atoms, e.g. benzenesulphonyloxy, p-toluenesulphonyloxy, 1-naphthalenesulphonyloxy or 2-naphthalenesulphonyloxy.

The radical W is preferably 1,5-dimethylpentamethylene; also suitable are 1-, 2- or 3-methylpentamethylene; 1,1-, 1,2-, 1,3-, 1,4-, 2,2-, 2,3-, 2,4- or 3,3-dimethylpentamethylene; 1,1,2-, 1,1,3-, 1,1,4-, 1,1,5-, 1,2,2-, 1,2,3-, 1,2,4-, 1,2,5-, 1,3,3-, 1,3,4-, 1,3,5- or 1,4,4-trimethylpentamethylene; 1,1,5,5-tetramethylpentamethylene; 1-, 2- or 3-ethylpentamethylene; 1,5-diethylpentamethylene or 1-methyl-5-ethylpentamethylene; and furthermore (when R² = R³ = H) also 1- or 2-methyl-3-oxapentamethylene; 1,1-, 1,2-, 1,4-, 1,5-, 2,2- or 2,4-dimethyl-3-oxapentamethylene; 1- or 2-ethyl-3-oxopentamethylene, 1,5-diethyl-3-oxapentamethylene and the like; and (when R² and/or R³ are CH₃) also unbranched tetramethylene, pentamethylene, hexamethylene, 3-oxapentamethylene, 2-hydroxypentamethylene or 3-hydroxypentamethylene.

The radical M is preferably MgCl, MgBr, MgI or Li.

The group E is preferably piperidinocarbonyl or oxopiperidinomethyl which is monosubstituted or polysubstituted by alkyl having 1–4 C atoms, preferably methyl, (for example 2-, 3- or 4-methylpiperidinocarbonyl, dimethylpiperidinocarbonyl, especially 2,6- or 3,5-dimethylpiperidinocarbonyl; trimethylpiperidinocarbonyl or tetramethylpiperidinocarbonyl, such as 2,2,6,6-tetramethylpiperidinocarbonyl, 2-methyl-3-, -4-, -5-or -6-oxopiperidinomethyl; 3-methyl-2-, -4-, -5- or -6-oxopiperidinomethyl; 4-methyl-2-oxopiperidinomethyl or 4-methyl-3-oxopiperidinomethyl; 2,6-dimethyl-3-oxopiperidinomethyl or 2,6-dimethyl-4-oxopiperidinomethyl; 3,5-dimethyl-2-oxopiperidinomethyl or 3,5-dimethyl-4-oxopiperidinomethyl; 2,2,6,6-tetramethyl-3-oxopiperidinomethyl or 2,2,6,6-tetramethyl-4-oxopiperidinomethyl); furthermore (when R² = R³ = H) also morpholinocarbonyl or oxomorpholinomethyl which is monosubstituted or polysubstituted by alkyl having 1–4 C atoms, preferably methyl, such as 2- or 3-methylmorpholinocarbonyl, 2,2-, 2,3-, 2,5-, 2,6-, 3,3- or 3,5-dimethylmorpholinocarbonyl, 2-methyl-3-, -5- or -6-oxomorpholinomethyl or 2,6-dimethyl-3-oxomorpholinomethyl; furthermore (when R² and/or R³ are CH₃) also piperidinocarbonyl, pyrrolidinocarbonyl, homopiperidinocarbonyl, morpholinocarbonyl, 3- or 4-hydroxypiperidinocarbonyl, 2-, 3- or 4-oxopiperidinomethyl, 2- or 3-oxopyrrolidinomethyl, 2-, 3- or 4-oxohomopiperidinomethyl or 2- or 3-oxomorpholinomethyl.

The starting materials for the process according to the invention are either known or can be prepared in analogy to known compounds by methods which are in themselves known from the literature. For example, the compounds II can be obtained by reacting the phenols of the formula R-OH (IV) with compounds of the formula X—CR²R³—Y, e.g. epibromohydrin, epichlorohydrin or 3-bromo-3-methyl-1,2-epoxybutane. Epoxides or halohydrins of Formula II are obtained here, depending on the method of working up; the epoxides have the advantage that they can be purified particularly easily. In general, the amines III and the phenols IV are known. The amino compounds V can be obtained from compounds of the formula X—CH₂—Y¹ and the amines H—Z (III). The aminoalcohols VI can be obtained in various ways, for example by reacting compounds of Formula II with potassium phthalimide and subsequently hydrolyzing. In general, the compounds VII and IX are known. The compounds VIII and X can be obtained from the phenols of the formula R-OH and aminoketones of the formula X—CR²R³—CO—CH₂—Z or compounds of the formula X—CR²R³—CR¹(OH)—E, respectively.

The reaction of the compounds II with the amines III is carried out in the presence or absence of an additional inert solvent at temperatures between about 0° and 200° C., preferably between about 50° and 120° C. Suitable inert solvents are those which are known from the literature for aminations of this kind and include but are not limited to alcohols, e.g. methanol, ethanol, isopropanol or n-butanol; ethers, e.g. diethyl ether, diisopropyl ether, tetrahydrofuran (THF) or dioxan; hydrocarbons, e.g. benzene, toluene or xylene; and sulphoxides, e.g. dimethylsulphoxide (DMSO). The amines III are preferably used in a molar ratio of at least 1:1 or in a molar excess relative to the compounds II; if they are used in sufficient excess, they can simultaneously act as the solvent. If the starting materials are compounds II which are so constituted that one mol of acid is eliminated in the reaction (if, for example, halohydrins are used, so that hydrogen halide is eliminated), it is preferably to employ either an additional base or an excess of the base III. Suitable additional bases include but are not limited to sodium carbonate, potassium carbonate, sodium bicarbonate or potassium bicarbonate. The reaction times required are between about 10 minutes and 7 days, depending on the starting materials used and the reaction temperature. It is also possible to employ elevated pressure and to accelerate the reaction in this way.

The compounds I can also be obtained in accordance with methods which are in themselves known and are described in the literature, e.g. by reacting the phenols R—OH (IV) with the amino compounds Y¹—CH₂—Z (V). For example, the phenol IV can first be converted into a salt, particularly a metal salt, for example an alkali metal salt (a Li salt, Na salt or K salt). The phenol can be reacted with a reagent which forms metal salts, for example an alkali metal (for example Na), an alkali metal hydride or amide (for example LiH or NaH, or $NaNH_2$ or $KNH_2$), a lower alcoholate of an alkali metal wherein the alcohol portion preferably contains 1-4 C atoms, e.g. lithium methylate, ethylate or tert.-butylate, sodium methylate, ethylate or tert.-butylate, potassium methylate, ethylate or tert.-butylate, etc., an organometallic compound (for example butyl-lithium, phenyl-lithium or phenyl-sodium) or a hydroxide, carbonate or bicarbonate of a metal (for example of Li, Na, K or Ca). The preparation of the phenolate is advantageously carried out in the presence of an inert solvent or mixture of solvents. Suitable solents are well known in the art and include but are not limited to hydrocarbons, e.g. hexane, benzene, toluene or xylene, ethers, e.g. diethyl ether, diisopropyl ether, THF, dioxane or diethylene glycol dimethyl ether; amides, e.g. dimethylformamide (DMF); alcohols, e.g. methanol or ethanol; and ketones, e.g. acetone or butanone.

The phenol IV or a salt thereof is preferably reacted with the compound V in the presence of a diluent, for example the solvent which has been used for the preparation of the salt, which can however be replaced by another solvent or diluted with another solvent. The reaction is generally carried out at temperatures between about $-20°$ and $150°$ C., preferably between $20°$ and $120°$ C.

The phenolate can also be formed in situ. In this case, the phenol IV and the compound V are allowed to react with one another in the presence of a base. A particularly preferred method consists in heating the compounds IV and V for about 5 to 15 hours, together with an aqueous alcoholic solution of sodium hydroxide.

It is also possible to react a primary amine VI with a compound VII in order to prepare the compounds I.

Suitable compounds of the formula VII include but are not limited to 1-,2- or 3-methyl-1,5-pentanediol and reactive esters thereof (e.g. alkyl or arylsulphonic acid esters thereof wherein alkyl is of 1-6 and aryl is of 6-10 C atoms) such as the bis-p-toluenesulphonates thereof; of 1-, 2- or 3-methyl-1,5-dichloropentane, 1-, 2- or 3-methyl-1,5-dibromopentane and 1-, 2- or 3-methyl-1,5-diiodopentane; 2,6-heptanediol and reactive esters thereof; 2,6-dichloro-, 2,6-dibromo- and 2,6-diiodo-heptane; 2,4-dimethyl-1,5-pentanediol and reactive esters thereof;
2,4-dimethyl-1,5-dichlorohexane, 2,4-dimethyl-1,5-dibromohexane, 2,4-dimethyl-1,5-diiodohexane and the like; and, if $R^2$ and/or $R^3$ is methyl, also 1,4-butanediol, 1,5-pentanediol, 1,6-hexanediol and 3-oxapentane-1,5-diol and reactive esters thereof; 1,4-dichlorobutane, 1,4-dibromobutane and 1,4-diiodobutane; 1,5-dichloropentane, 1,5-dibromopentane and 1,5-diiodopentane; 1,6-dichlorohexane, 1,6-dibromohexane and 1,6-diiodohexane; 1,5-dichloro-3-oxapentane, 1,5-dibromo-3-oxapentane and 1,5-diiodo-3-oxapentane.

In this reaction it is preferable to react calculated quantities of the reactants in the presence of a solvent. Suitable solvents are well known and include but are not limited to water; aliphatic alcohols, e.g. methanol, ethanol, isopropanol or n-butanol; glycols, e.g. ethylene glycol; ethers, e.g. diethyl ether or diisopropyl ether, THF or dioxane; aliphatic hydrocarbons, e.g. petroleum ether or hexane; aromatic hydrocarbons, e.g. benzene, toluene or xylene; halogenated hydrocarbons, e.g. chloroform or chlorobenzene; nitriles, e.g. acetonitrile; amides, e.g. DMF or dimethylacetamide; sulphoxides, e.g. DMSO; or mixtures of these solvents. The reaction temperatures are generally between about 0° and about 300° C., preferably between 20° C. and the boiling point of the solvent used, which can, if desired, be raised by using pressure (up to about 200 atmospheres, generally 1-10 atmospheres gauge).

Generally, an acid is split off in the reaction; it is therefore preferable to carry out the reaction in the presence of an inorganic or organic base, for example in the presence of an alkali metal hydroxide, carbonate or alcoholate or alkaline earth metal hydroxide, carbonate or alcoholate such as sodium hydroxide, carbonate or ethylate or potassium hydroxide, carbonate or ethylate, or of a tertiary base, such as triethylamine, pyridine, picoline or quinoline.

If X is a hydroxy, alkoxy, alkanoyloxy, alkylsulphonyloxy or arylsulphonyloxy group, it can also be advisable to add an acid catalyst, for example an inorganic acid such as sulphuric acid, polyphosphoric acid, hydrobromic acid or hydrochloric acid and/or an organic acid such as formic acid, acetic acid, propionic acid or p-toluenesulphonic acid. An excess of the acid can also simultaneously act as the solvent.

In order to prepare the compounds I, it is furthermore possible to convert the keto group of an aminoketone VIII into a CHOH group using a reducing agent or into a $C(CH_3)OH$ group using an organometallic reagent IX.

Suitable reducing agents are all those which are capable of reducing carbonyl groups to alcohol groups in accordance with methods known from the literature. Complex metal hydrides are generally preferred. It is also possible to reduce the carbonyl group with the aid of catalytically activated hydrogen or nascent hydrogen.

Among the complex metal hydrides, sodium borohydride and lithium aluminum hydride are preferred. It is preferable to carry out the reaction in one of the customary solvents, e.g. when using $NaBH_4$ preferably in an alcohol such as methanol or ethanol, and when using $LiAlH_4$ preferably in an ether such as diethyl ether or di-n-butyl ether, THF or ethylene glycol dimethyl ether. The reaction temperatures are generally between about $-80°$ and $150°$ C., preferably between about $15°$ C. and the boiling point of the solvent used.

Suitable catalysts for catalytic hydrogenations are well known in the art and include but are not limited to noble metal catalysts, nickel and/or cobalt catalysts and also mixed catalysts, such as copper-chromium oxide. The noble metal catalysts can be present on supports (for example platinum or palladium on charcoal or palladium on calcium carbonate or strontium carbonate), in the form of oxide catalysts (for example platinum oxide) or in the form of a finely divided metal. Nickel and cobalt catalysts are preferably employed in the form of Raney metals and nickel is also suitably employed on kieselguhr or punice as a support. Hydrogenation can be carried out at room temperature and normal pressure or at elevated temperature and/or elevated pressure. It is preferable to carry out the reaction at elevated pressures between 1 and 100 atmospheres and at temperatures between $-80°$ and $+150°$ C., preferably between room temperature and $+100°$ C. The reaction can be carried out in the acid, neutral or basic range and preferably in the presence of a solvent such as water, methanol, ethanol, isopropanol, n-butanol, ethyl acetate, dioxane, acetic acid or THF; mixtures of these solvents with one another can also be used. Copper-chromium oxide and Raney metals are preferred catalysts in the catalytic hydrogenation of the aminoketones VIII.

If nascent hydrogen is used as the reducing agent, it can be generated by methods known in the art, e.g. by treating metals with acids or bases. Thus it is possible to use, for example, a mixture of zinc with acid or alkali metal hydroxide solution, of iron with hydrochloric acid or acetic acid or of tin with hydrochloric acid. The use of sodium or another alkali metal in an alcohol, e.g. ethanol, isopropanol, butanol, amyl alcohol, isoamyl alcohol or phenol, is also suitable. An aluminum-nickel alloy in an aqueous alkaline solution, if necessary with the addition of ethanol, can also be used. Sodium amalgam or aluminum amalgam in an aqueous-alcoholic or aqueous solution are also suitable for generating the nascent hydrogen. The reaction can also be carried out in a heterogeneous phase, preferably comprising an aqueous phase and a benzene or toluene phase. The reaction temperatures employed are suitably between room temperature and the boiling point of the solvent used.

Suitable organometallic compounds of the formula IX are primarily methyl-magnesium bromide, chloride and iodide and methyl-lithium. The aminoketones VIII are generally reacted with the organometallic compounds IX by adding a solution of the aminoketone slowly, if appropriate with cooling, to a solution of the organometallic compound and then warming or boiling the resulting mixture until the reaction is complete. Suitable solvents are known in the art and include but are not limited to ethers, e.g. diethyl ether, diisopropyl ether, THF, anisole, dibenzyl ether or dioxane; hydrocarbons, e.g. benzene or toluene; chlorinated hydrocarbons, e.g. methylene chloride; as well as higher ethers or hydrocarbons as well as mixtures of these solvents with one another. In some cases it is advisable to add inorganic salts, such as magnesium bromide or copper(I) chloride. The reaction time and temperature are not critical; generally, however, the reaction is carried out at temperatures between 0° C. and the boiling point of the solvent used and is complete after ½ to 48 hours, preferably after boiling for 4 to 6 hours. Working up is carried out by hydrolyzing the mixture, e.g. using water, dilute acids or ammonium chloride solution, and then isolating the bases or their salts.

The compounds I can, furthermore, be obtained by the reduction of the amides, lactams or aminoketones X, which is also carried out in accordance with methods which are in themselves known from the literature. The amides and lactams are preferably reduced with LiAlH$_4$ under the conditions indicated above. The carbonyl groups in the aminoketones are, however, preferably reduced to CH$_2$ groups by the Clemmensen or Wolff-Kishner methods.

In the Clemmensen reduction, the carbonyl compounds are treated, for example, with a mixture of zinc and hydrochloric acid, amalgamated zinc and hydrochloric acid or tin and hydrochloric acid, either in an aqueous alcoholic solution or in a heterogeneous phase such as a mixture of water and benzene or toluene. The Wolff-Kishner reduction can be carried out by treating the carbonyl compounds with anhydrous hydrazine in absolute ethanol in an autoclave or bomb tube, and the reaction temperatures can be raised to 250° C. It is advantageous to use sodium ethylate as the catalyst. The reduction can also be varied by reacting with hydrazine hydrate as the reducing agent in a high-boiling, water-miscible solvent such as diethylene glycol or triethylene glycol, and in the presence of alkali, e.g. sodium hydroxide. The reaction mixture is generally boiled for about 3-4 hours. The water is then distilled off and the hydrazone formed is decomposed at temperatures of up to about 200° C. The reduction can, however, also be carried out at room temperature using hydrazine in DMSO.

A base of the Formula I can be converted into the appropriate acid addition salt in the customary manner by neutralization with an acid. Generally, acids which produce physiologically acceptable salts will be used for this reaction, although other acids can be used to facilitate isolation and/or characterization. Suitable acids are well known in the art and include but are not limited to inorganic acids, e.g. sulphuric acid, nitric acid, hydrogen halide acids such as hydrochloric acid or hydrobromic acid, phosphoric acids such as orthophosphoric acid. Also suitable are organic aliphatic, alicyclic, araliphatic, aromatic or heterocyclic, monobasic or polybasic carboxylic or sulphonic acids. Suitable such organic acids include but are not limited to formic acid, acetic acid, propionic acid, pivalic acid, diethylacetic acid, oxalic acid, malonic acid, succinic acid, pimelic acid, fumaric acid, maleic acid, lactic acid, tartaric acid, malic acid; aminocarboxylic acids; sulphamic acid, benzoic acid, salicyclic acid, phenylpropionic acid, citric acid, gluconic acid, ascorbic acid, isonicotinic acid, methanesulphonic or ethanesulphonic acid, ethanedisulphonic acid, 2-hydroxyethanesulphonic acid, benzenesulphonic acid, p-toluenesulphonic acid and naphthalenemonosulphonic and naphthalenedisulphonic acids. If desired, the free bases of the Formula I can be liberated from their salts by treatment with strong bases, such as sodium or potassium hydroxide or sodium or potassium carbonate.

If the compounds of Formula I contain a center of asymmetry, they are usually present in a racemic form. If the compounds have two or more centers of asymmetry, they are generally obtained from the synthesis as mixtures of racemates from which the individual racemates can be isolated and obtained in a pure form, for example by repeated recrystallization from suitable solvents.

Racemates obtained can be resolved into their optical antipodes by mechanical or chemical means in accordance with methods which are known in the art. It is preferable to form diastereomers from the racemic mixture by reaction with an optically active resolving agent. Examples of suitable resolving agents are optically active acids, e.g. D- and L-tartaric acid, dibenzoyl-D- and dibenzoyl-L-tartaric acid, diacetyl-D- and diacetyl-L-tartaric acid, β-camphorsulphonic acid, D- and L-mandelic acid, D- and L-malic acid or D- and L-lactic acid. It is of course possible to obtain optically active compounds by the methods described by using starting materials which are already optically active.

Due to their lipoprotein lowering activity, the compounds of this invention are useful as serum cholesterol and triglyceride lowering agents in human and veterinary medicine. These compounds are also effective fibrinolytic and thrombocyte aggregationinhibiting agents. In addition to their use in vitro, they can be employed, for example, in the enteral or parenteral therapy of hematogeneous thrombo-embolisms in substantially the same manner as the known compounds acetylsalicylic acid or indomethacin. Furthermore, β-receptor blocking and neuroleptic activity of these compounds render them useful in the enteral or parenteral therapy of certain circulation disorders in substantially the same manner as the known compound 1-(indolyl-4-oxy)-3-isopropylamino-2-propanol.

The compounds of this invention can be employed in mixture with conventional excipients, i.e. pharmaceutically acceptable organic or inorganic substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrolidone, etc. The pharmaceutical preparations can be sterilized and if desired mixed with auxiliary agents, e.g. lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g. by microencapsulation, multiple coatings, etc.

Generally, the compounds of this invention are dispensed in unit dosage form comprising 1–5,000 mg. of a pharmaceutical carrier per each unit dosage and the amount of active agent of the invention per unit dosage is about 50–2,000 mg., preferably about 100–500 mg.

The compounds of this invention are generally administered to animals, including but not limited to mammals, e.g. humans. A lipoprotein lowering effective daily dosage of the active compounds as administered orally to humans generally comprises about 0.2 to 100, preferably 1 to 40 mg./kg., together with 1 to 5,000 mg. of pharmaceutically acceptable carrier. The dose can be administered singly or as divided dosages throughout the day.

Oral administration is preferred, the compounds of this invention being particularly valuable in the treatment of humans afflicted with elevated serum cholesterol and/or triglyceride levels. In this regard, they can be employed in substantially the same manner as the known compound clofibrate.

It will be appreciated that the actual preferred amounts of active compounds used will vary according to the specific compound being utilized, the particular compositions formulated, the mode of application, and the particular situs and organism being treated. Optimal application rates for a given set of conditons can be ascertained by those skilled in the art using conventional dosage determination tests in view of the above quidelines.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

All the compounds of Formula I shown in the following Examples are particularly suitable for the production of pharmaceutical preparations.

EXAMPLE 1

A solution of 22.6 g of 1-(biphenylyl-4-oxy)-2,3-epoxypropane and 25 g of 2,6-dimethylpiperidine in 150 ml of ethanol is boiled for 15 hours and evaporated. The resulting 1-(biphenylyl-4-oxy)-3-(2,6-dimethylpiperidino)-2-propanol is recrystallised from isopropanol. M.p. 110°–111°.

EXAMPLE 2 to 20

The following are obtained analogously to Example 1 using the corresponding amines (for example 2-, 3- or 4-methylpiperidine and the like):

2. 1-(Biphenylyl-4-oxy)-3-(2-methylpiperidino)-2-propanol, m.p. 114°–115°.
3. 1-(Biphenylyl-4-oxy)-3-(3-methylpiperidino)-2-propanol, m.p. 104°.
4. 1-(Biphenylyl-4-oxy)-3-(4-methylpiperidino)-2-propanol, m.p. 81.5°–82°.
5. 1-(Biphenylyl-4-oxy)-3-(2,2-dimethylpiperidino)-2-propanol.
6. 1-(Biphenylyl-4-oxy)-3-(2,3-dimethylpiperidino)-2-propanol.
7. 1-(Biphenylyl-4-oxy)-3-(2,4-dimethylpiperidino)-2-propanol.
8. 1-(Biphenylyl-4-oxy)-3-(2,5-dimethylpiperidino)-2-propanol.
9. 1-(Biphenylyl-4-oxy)-3-(3,3-dimethylpiperidino)-2-propanol.
10. 1-(Biphenylyl-4-oxy)-3-(3,4-dimethylpiperidino)-2-propanol.
11. 1-(Biphenylyl-4-oxy)-3-(3,5-dimethylpiperidino)-2-propanol.
12. 1-(Biphenylyl-4-oxy)-3-(4,4-dimethylpiperidino)-2-propanol.
13. 1-(Biphenylyl-4-oxy)-3-(2,2,3-trimethylpiperidino)-2-propanol.
14. 1-(Biphenylyl-4-oxy)-3-(2,2,6,6-tetramethylpiperidino)-2-propanol, m.p. 87°–88°. Hydrochloride, m.p. 232°–234°.
15. 1-(Biphenylyl-4-oxy)-3-(4-ethylpiperidino)-2-propanol.
16. 1-(Biphenylyl-4-oxy)-3-(4-n-butylpiperidino)-2-propanol.
17. 1-(Biphenylyl-4-oxy)-3-(2-methyl-6-ethylpiperidino)-2-propanol.
18. 1-(Biphenylyl-4-oxy)-3-(2-methylmorpholino)-2-propanol.
19. 1-(Biphenylyl-4-oxy)-3-(3-methylmorpholino)-2-propanol.
20. 1-(Biphenylyl-4-oxy)-3-(2,6-dimethylmorpholino)-2-propanol, m.p. 133°–134°.

EXAMPLES 21 to 38

The following are obtained from 1,2-epoxy-3-(biphenylyl-4-oxy)-butane or from 1,2-epoxy-3-(biphenylyl-4- oxy)-3-methylbutane analogously to Example 1, using the corresponding amines:

21. 2-(Biphenylyl-4-oxy)-4-piperidino-3-butanol.
22. 2-(Biphenylyl-4-oxy)-4-morpholino-3-butanol.
23. 2-(Biphenylyl-4-oxy)-4-pyrrolidino-3-butanol.
24. 2-(Biphenylyl-4-oxy)-4-homopiperidino-3-butanol.
25. 2-(Biphenylyl-4-oxy)-4-(4-methylpiperidino)-3-butanol.
26. 2-(Biphenylyl-4-oxy)-4-(2,6-dimethylpiperidino)-3-butanol.
27. 2-(Biphenylyl-4-oxy)-4-(3,5-dimethylpiperidino)-3-butanol.
28. 2-(Biphenylyl-4-oxy)-4-(3-hydroxypiperidino)-3-butanol.
29. 2-(Biphenylyl-4-oxy)-4-(4-hydroxypiperidino)-3-butanol.
30. 2-(Biphenylyl-4-oxy)-2-methyl-4-piperidino-3-butanol, m.p. 105°–107°; hydrochloride, m.p. 182°–183°.
31. 2-(Biphenylyl-4-oxy)-2-methyl-4-morpholino-3-butanol, m.p. 101°–103°; hydrochloride, m.p. 237°.
32. 2-(Biphenylyl-4-oxy)-2-methyl-4-pyrrolidino-3-butanol.
33. 2-(Biphenylyl-4-oxy)-2-methyl-4-homopiperidino-3-butanol, $n_D^{20}$ 1.5700. Hydrochloride, m.p. 167°–169°.
34. 2-(Biphenylyl-4-oxy)-2-methyl-4-(4-methylpiperidino)-3-butanol, m.p. 85°–87°; hydrochloride, m.p. 180°–182°.
35. 2-(Biphenylyl-4-oxy)-2-methyl-4-(2,6-dimethylpiperidino)-3-butanol, m.p. 91°–94°; hydrochloride, m.p. 200°–202°.
36. 2-(Biphenylyl-4-oxy)-2-methyl-4-(3,5-dimethylpiperidino)-3-butanol.
37. 2-(Biphenylyl-4-oxy)-2-methyl-4-(3-hydroxypiperidino)-3-butanol.
38. 2(Biphenylyl-4-oxy)-2-methyl-4-(4-hydroxpiperidino)-3-butanol.

EXAMPLES 39 to 50

The following are obtained from 1-(4'-fluorobiphenylyl-4-oxy)-2,3-epoxypropane, 1-(4'-chlorobiphenylyl-4-oxy)-2,3-epoxypropane, 1-(4'-bromobiphenylyl-4-oxy)-2,3-epoxypropane or 1-(4'-trifluoromethylbiphenylyl-4-oxy)-2,3-epoxypropane, analogously to Example 1:

39. 1-(4'-Fluorobiphenylyl-4-oxy)-3-(4-methylpiperidino)-2-propanol, m.p. 92°–93°.
40. 1-(4'-Fuorobiphenylyl-4-oxy)-3-(2,6-dimethylpiperidino)-2-propanol.
41. 1-(4'-Fluorobiphenylyl-4-oxy)-3-(3,5-dimethylpiperidino)-2-propanol.
42. 1-(4'-Chlorobiphenylyl-4-oxy)-3-(4-methylpiperidino)-2-propanol, m.p. 108°–109°.
43. 1-(4'-Chlorobiphenylyl-4-oxy)-3-(2,6-dimethylpiperidino)-2-propanol.
44. 1-(4'-Chlorobiphenylyl-4-oxy)-3-(3,5-dimethylpiperidino)-2-propanol.
45. 1-(4'-Bromobiphenylyl-4-oxy)-3-(4-methylpiperidino)-2-propanol.
46. 1-(4'-Bromobiphenylyl-4-oxy)-3-(2,6-dimethylpiperidino)-2-propanol.
47. 1-(4'-Bromobiphenylyl-4-oxy)-3-(3,5-dimethylpiperidino)-2-propanol.
48. 1-(4'-Trifluoromethylbiphenylyl-4-oxy)-3-(4-methylpiperidino)-2-propanol, m.p. 121°–122°.
49. 1-(4'-Trifluoromethylbiphenylyl-4-oxy)-3-(2,6-dimethylpiperidino)-2-propanol, m.p. 126°–127°.
50. 1-(4'-Trifluoromethylbiphenylyl-4-oxy)-3-(3,5-dimethylpiperidino)-2-propanol.

EXAMPLES 51 to 106

Starting from:

1,2-Epoxy-3-(4'-fluorobiphenylyl-4-oxy)-butane,
1,2-epoxy-3-(4'-fluorophenylyl-4-oxy)-3-methylbutane,
1,2-epoxy-3-(4'-chlorobiphenylyl-4-oxy)-butane,
1,2-epoxy-3-(4'-chlorobiphenylyl-4-oxy)-3-methylbutane,
1,2-epoxy-3-(4'-bromobiphenylyl-4-oxy)-butane,
1,2-epoxy-3-(4'-bromobiphenylyl-4-oxy)-3-methylbutane,
1,2-epoxy-3-(4'-trifluoromethylbiphenylyl-4-oxy)-butane and
1,2-epoxy-3-(4'-trifluoromethylbiphenyl-4-oxy)-3-methylbutane the following are obtained, analogously to Example 1, using the corresponding amines:

51. 2-(4'-Fluorobiphenylyl-4-oxy)-4-piperidino-3-butanol.
52. 2-(4'-Fluorobiphenylyl-4-oxy)-4-morpholino-3-butanol.
53. 2-(4'-Fluorobiphenylyl-4-oxy)-4-pyrrolidino-3-butanol.
54. 2-(4'-Fluorobiphenylyl-4-oxy)-4-homopiperidino-3-butanol.
55. 2-(4'-Fluorobiphenylyl-4-oxy)-4-(4-methylpiperidino)-3-butanol.
56. 2-(4'-Fluorobiphenylyl-4-oxy)-4-(2,6-dimethylpiperidino)-3-butanol.
57. 2-(4'-Fluorobiphenyly-4-oxy)-4-(3,5-dimethylpiperidino)-3-butanol.
58. 2-(4'-Fluorobiphenylyl-4-oxy)-2-methyl-4-piperidino-3-butanol.
59. 2-(4'-Fluorobiphenylyl-4-oxy)-2-methyl-4-morpholino-3-butanol.
60. 2-(4'-Fluorobiphenylyl-4-oxy)-2-methyl-4-pyrrolidino-3-butanol.
61. 2-(4'-Fluorobiphenylyl-4-oxy)-2-methyl-4-homopiperidino-3-butanol.
62. 2-(4'-Fluorobiphenylyl-4-oxy)-2-methyl-4-(4-methylpiperidino)-3-butanol.
63. 2-(4'-Fluorobiphenylyl-4-oxy)-2-methyl-4-(2,6-dimethylpiperidino)-3-butanol.
64. 2-(4'-Fluorobiphenylyl-4-oxy)-2-methyl-4-(3,5-dimethylpiperidino)-3-butanol.
65. 2-(4'-Chlorobiphenylyl-4-oxy)-4-piperidino-3-butanol.
66. 2-(4'-Chlorobiphenylyl-4-oxy)-4-morpholino-3-butanol.
67. 2-(4'-Chlorobiphenylyl-4-oxy)-4-pyrrolidino-3-butanol.
68. 2-(4'-Chlorobiphenylyl-4-oxy)-4-homopiperidino-3-butanol.
69. 2-(4'-Chlorobiphenylyl-4-oxy)-4-(4-methylpiperidino)-3-butanol.
70. 2-(4'-Chlorophenylyl-4-oxy)-4-(2,6-dimethylpiperidino)-3-butanol.
71. 2-(4'-Chlorobiphenylyl-4-oxy)-4-(3,5-dimethylpiperidino)-3-butanol.
72. 2-(4'-Chlorobiphenylyl-4-oxy)-2-methyl-4-piperidino-3-butanol.
73. 2-(4'-Chlorobiphenylyl-4-oxy)-2-methyl-4-morpholino-3-butanol.

74. 2-(4'-Chlorobiphenylyl-4-oxy)-2-methyl-4-pyrrolidino-3-butanol.
75. 2-(4'-Chlorobiphenylyl-4-oxy)-2-methyl-4-homopiperidino-3-butanol.
76. 2-(4'-Chlorobiphenylyl-4-oxy)-2-methyl-4-(4-methylpiperidino)-3-butanol.
77. 2-(4'-Chlorobiphenylyl-4-oxy)-2-methyl-4-(2,6-dimethylpiperidino)-3-butanol.
78. 2-(4'-Chlorobiphenylyl-4-oxy)-2-methyl-4-(3,5-dimethylpiperidino)-3-butanol.
79. 2-(4'-Bromobiphenylyl-4-oxy)-4-piperidino-3-butanol.
80. 2-(4'-Bromobiphenylyl-4-oxy)-4-morpholino-3-butanol.
81. 2-(4'-Bromobiphenylyl-4-oxy)-4-pyrrolidino-3-butanol.
82. 2-(4'-Bromobiphenylyl-4-oxy)-4-homopiperidino-3-butanol.
83. 2-(4'-Bromobiphenylyl-4-oxy)-4-(4-methylpiperidino)-3-butanol.
84. 2-(4'-Bromobiphenylyl-4-oxy)-4-(2,6-dimethylpiperidino)-3-butanol.
85. 2-(4'-Bromobiphenylyl-4-oxy)-4-(3,5-dimethylpiperidino)-3-butanol.
86. 2-(4'-Bromobiphenylyl-4-oxy)-2-methyl-4-piperidino-3-butanol.
87. 2-(4'-Bromobiphenylyl-4-oxy)-2-methyl-4-morpholino-3-butanol.
88. 2-(4'-Bromobiphenylyl-4-oxy)-2-methyl-4-pyrrolidino-3-butanol.
89. 2-(4'-Bromobiphenylyl-4-oxy)-2-methyl-4-homopiperidino-3-butanol.
90. 2-(4'-Bromobiphenylyl-4-oxy)-2-methyl-4-(4-methylpiperidino)-3-butanol.
91. 2-(4'-Bromobiphenylyl-4-oxy)-2-methyl-4-(2,6-dimethylpiperidino)-3-butanol.
92. 2-(4'-Bromobiphenylyl-4-oxy)-2-methyl-4-(3,5-dimethylpiperidino)-3-butanol.
93. 2-(4'-Trifluoromethylbiphenylyl-4-oxy)-4-piperidino-3-butanol.
94. 2-(4'-Trifluoromethylbiphenylyl-4-oxy)-4-morpholino-3-butanol.
95. 2-(4'-Trifluoromethylbiphenylyl-4-oxy)-4-pyrrolidino-3-butanol.
96. 2-(4'-Trifluoromethylbiphenylyl-4-oxy)-4-homopipridino-3-butanol.
97. 2-(4'-Trifluoromethylbiphenyl-4-oxy)-4-(4-methylpiperidino)-3-butanol.
98. 2-(4'-Trifluoromethylbiphenylyl-4-oxy)-4-(2,6-dimethylpiperidino)-3-butanol.
99. 2-(4'-Trifluoromethylbiphenylyl-4-oxy)-4-(3,5-dimethylpiperidino)-3-butanol.
100. 2-(4'-Trifluoromethylbiphenyl-4-oxy)-2-methyl-4-piperidino-3-butanol.
101. 2-(4'-Trifluoromethylbiphenylyl-4-oxy)-2-methyl-4-morpholino-3-butanol.
102. 2-(4'-Trifluoromethylbiphenylyl-4-oxy)-2-methyl-4-pyrrolidino-3-butanol.
103. 2-(4'-Trifluoromethylbiphenylyl-4-oxy)-2-methyl-4-homopiperidino-3-butanol.
104. 2-(4'-Trifluoromethylbiphenylyl-4-oxy)-2-methyl-4-(4-methylpiperidino)-3-butanol.
105. 2-(4'-Trifluoromethylbiphenylyl-4-oxy)-2-methyl-4-(2,6-dimethylpiperidino)-3-butanol.
106. 2-(4'-Trifluoromethylbiphenylyl-4-oxy)-2-methyl-4-(3,5-dimethylpiperidino)-3-butanol.

EXAMPLES 107 TO 121

The following are obtained, analogously to Example 1, from 1-(biphenylyl-4-oxy)-2,3-epoxy-2-methylpropane or the 4'-fluoro, 4'-chloro, 4'-bromo or 4'-trifluoromethyl derivatives thereof:

107. 1-(Biphenylyl-4-oxy)-2-methyl-3-(4-methylpiperidino)-2-propanol.
108. 1-(Biphenylyl-4-oxy)-2-methyl-3-(2,6-dimethylpiperidino)-2-propanol.
109. 1-(Biphenylyl-4-oxy)-2-methyl-3-(3,5-dimethylpiperidino)-2-propanol.
110. 1-(4'-Fluorobiphenylyl-4-oxy)-2-methyl-3-(4-methylpiperidino)-2-propanol.
111. 1-(4'-Fluorobiphenylyl-4-oxy)-2-methyl-3-(2,6-dimethylpiperidino)-2-propanol.
112. 1-(4'-Fluorobiphenylyl-4-oxy)-2-methyl-3-(3,5-dimethylpiperidino)-2-propanol.
113. 1-(4'-Chlorobiphenylyl-4-oxy)-2-methyl-3-(4-methylpiperidino)-2-propanol.
114. 1-(4'-Chlorobiphenylyl-4-oxy)-2-methyl-3-(2,6-dimethylpiperidino)-2-propanol.
115. 1-(4'-Chlorobiphenylyl-4-oxy)-2-methyl-3-(3,5-dimethylpiperidino)-2-propanol.
116. 1-(4'-Bromobiphenylyl-4-oxy)-2-methyl-3-(4-methylpiperidino)-2-propanol.
117. 1-(4'-Bromobiphenylyl-4-oxy)-2-methyl-3-(2,6-dimethylpiperidino)-2-propanol.
118. 1-(4'-Bromobiphenylyl-4-oxy)-2-methyl-3-(3,5-dimethylpiperidino)-2-propanol.
119. 1-(4'-Trifluoromethylbiphenylyl-4-oxy)-2-methyl-3-(4-methylpiperidino)-2-propanol.
120. 1-(4'-Trifluoromethylbiphenylyl-4-oxy)-2-methyl-3-(2,6-dimethylpiperidino)-2-propanol.
121. 1-(4'-Trifluoromethylbiphenylyl-4-oxy)-2-methyl-3-(3,5-dimethylpiperidino)-2-propanol.

EXAMPLES 122 TO 191

The following are obtained, analogously to Example 1, from 1,2-epoxy-2-methyl-3-(biphenylyl-4-oxy)-butane, 1,2-epoxy-2,3-dimethyl-3-(biphenylyl-4-oxy)-butane or the corresponding 4'-fluoro, 4'-chloro, 4'-bromo or 4'-trifluoromethyl derivatives:

122. 2-(Biphenylyl-4-oxy)-3-methyl-4-piperidino-3-butanol.
123. 2-(Biphenylyl-4-oxy)-3-methyl-4-morpholino-3-butanol.
124. 2-(Biphenylyl-4-oxy)-3-methyl-4-pyrrolidino-3-butanol.
125. 2-(Biphenylyl-4-oxy)-3-methyl-4-homopiperidino-3-butanol.
126. 2-(Biphenylyl-4-oxy)-3-methyl-4-(4-methylpiperidino)-3-butanol.
127. 2-(Biphenylyl-4-oxy)-3-methyl-4-(2,6-dimethylpiperidino)-3-butanol.
128. 2-(Biphenylyl-4-oxy)-3-methyl-4-(3,5-dimethylpiperidino)-3-butanol.
129. 2-(Biphenylyl-4-oxy)-2,3-dimethyl-4-piperidino-3-butanol, hydrochloride, m.p. 208°–210°.
130. 2-(Biphenylyl-4-oxy)-2,3-dimethyl-4-morpholino-3-butanol.
131. 2-(Biphenylyl-4-oxy)-2,3-dimethyl-4-pyrrolidino-3-butanol.
132. 2-(Biphenylyl-4-oxy)-2,3-dimethyl-4-homopiperidino-3-butanol.

133. 2-(Biphenylyl-4-oxy)-2,3-dimethyl-4-(4-methylpiperidino)-3-butanol, m.p. 51°–54°; hydrochloride, m.p. 198°–199°.
134. 2-(Biphenylyl-4-oxy)-2,3-dimethyl-4-(2,6-dimethylpiperidino)-3-butanol.
135. 2-(Biphenylyl-4-oxy)-2,3-dimethyl-4-(3,5-dimethylpiperidino)-3-butanol.
136. 2-(4'-Fluorobiphenylyl-4-oxy)-3-methyl-4-piperidino-3-butanol.
137. 2-(4'-Fluorobiphenylyl-4-oxy)-3-methyl-4-morpholino-3-butanol.
138. 2-(4'-Fluorobiphenylyl-4-oxy)-3-methyl-4-pyrrolidino-3-butanol.
139. 2-(4'-Fluorobiphenylyl-4-oxy)-3-methyl-4-homopiperidino-3-butanol.
140. 2-(4'-Fluorobiphenylyl-4-oxy)-3-methyl-4-(4-methylpiperidino)-3-butanol.
141. 2-(4'-Fluorobiphenylyl)-4-oxy)-3-methyl-4-(2,6-dimethylpiperidino)-3-butanol.
142. 2-(4'-Fluorobiphenylyl-4-oxy)-3-methyl-4-(3,5-dimethylpiperidino)-3-butanol.
143. 2-(4'-Fluorobiphenylyl-4-oxy)-2,3-dimethyl-4-piperidino-3-butanol.
144. 2-(4'-Fluorobiphenylyl-4-oxy)-2,3-dimethyl-4-morpholino-3-butanol.
145. 2-(4'-Fluorobiphenylyl-4-oxy)-2,3-dimethyl-4-pyrrolidino-3-butanol.
146. 2-(4'-Fluorobiphenylyl-4-oxy)-2,3-dimethyl-4-homopiperidino-3-butanol.
147. 2-(4'-Fluorobiphenylyl-4-oxy)-2,3-dimethyl-4-(4-methylpiperidino)-3-butanol.
148. 2-(4'-Fluorobiphenylyl-4-oxy)-2,3-dimethyl-4-(2,6-dimethylpiperidino)-3-butanol.
149. 2-(4'-Fluorobiphenylyl-4-oxy)-2,3-dimethyl-4-(3,5-dimethylpiperidino)-3-butanol.
150. 2-(4'-Chlorobiphenylyl-4-oxy)-3-methyl-4-piperidino-3-butanol.
151. 2-(4'-Chlorobiphenylyl-4-oxy)-3-methyl-4-morpholino-3-butanol.
152. 2-(4'-Chlorobiphenylyl-4-oxy)-3-methyl-4-pyrrolidino-3-butanol.
153. 2-(4'-Chlorobiphenylyl-4-oxy)-3-methyl-4-homopiperidino-3-butanol.
154. 2-(4'-Chlorobiphenylyl-4-oxy)-3-methyl-4-(4-methylpiperidino)-3-butanol.
155. 2-(4'-Chlorobiphenylyl-4-oxy)-3-methyl-4-(2,6-dimethylpiperidino)-3-butanol.
156. 2-(4'-Chlorobiphenylyl-4-oxy)-3-methyl-4-(3,5-dimethylpiperidino)-3-butanol.
157. 2-(4'-Chlorobiphenylyl-4-oxy)-2,3-dimethyl-4-piperidino-3-butanol.
158. 2-(4'-Chlorobiphenylyl-4-oxy)-2,3-dimethyl-4-morpholino-3-butanol.
159. 2-(4'-Chlorobiphenylyl-4-oxy)-2,3-dimethyl-4-pyrrolidino-3-butanol.
160. 2-(4'-Chlorobiphenylyl-4-oxy)-2,3-dimethyl-4-homopiperidino-3-butanol.
161. 2-(4'-Chlorobiphenylyl-4-oxy)-2,3-dimethyl-4-(4-methylpiperidino)-3-butanol.
162. 2-(4'-Chlorobiphenylyl-4-oxy)-2,3-dimethyl-4-(2,6-dimethylpiperidino)-3-butanol.
163. 2-(4'-Chlorobiphenyl-4-oxy)-2,3-dimethyl-4-(3,5-dimethylpiperidino)-3-butanol.
164. 2-(4'-Bromobiphenylyl-4-oxy)-3-methyl-4-piperidino-3-butanol.
165. 2-(4'-Bromobiphenylyl-4-oxy)-3-methyl-4-morpholino-3-butanol.
166. 2-(4'-Bromobiphenylyl-4-oxy)-3-methyl-4-pyrrolidino-3-butanol.
167. 2-(4'-Bromobiphenylyl-4-oxy)-3-methyl-4-homopiperidino-3-butanol.
168. 2-(4'-Bromobiphenylyl-4-oxy)-3-methyl-4-(4-methylpiperidino)-3-butanol.
169. 2-(4'-Bromobiphenylyl-4-oxy)-3-methyl-4-(2,6-dimethylpiperidino)-3-butanol.
170. 2-(4'-Bromobiphenylyl-4-oxy)-3-methyl-4-(3,5-dimethylpiperidino)-3-butanol.
171. 2-(4'-Bromobiphenylyl-4-oxy)-2,3-dimethyl-4-piperidino-3-butanol.
172. 2-(4'-Bromobiphenylyl-4-oxy)-2,3-dimethyl-4-morpholino-3-butanol.
173. 2-(4'-Bromobiphenylyl-4-oxy)-2,3-dimethyl-4-pyrrolidino-3-butanol.
174. 2-(4'-Bromobiphenylyl-4-oxy)-2,3-dimethyl-4-homopiperidino-3-butanol.
175. 2-(4'-Bromobiphenylyl-4-oxy)-2,3-dimethyl-4-(4-methylpiperidino)-3-butanol.
176. 2-(4'-Bromobiphenylyl-4-oxy)-2,3-dimethyl-4-(2,6-dimethylpiperidino)-3-butanol.
177. 2-(4'-Bromobiphenylyl-4-oxy)-2,3-dimethyl-4-(3,5-dimethylpiperidino)-3-butanol.
178. 2-(4'-Trifluoromethylbiphenlyl-4-oxy)-3-methyl-4-piperidino-3-butanol.
179. 2-(4'-Trifluoromethylbiphenylyl-4-oxy)-3-methyl-4-morpholino-3-butanol.
180. 2-(4'-Trifluoromethylbiphenyl-4-oxy)-3-methyl-4-pyrrolidino-3-butanol.
181. 2-(4'-Trifluoromethylbiphenylyl-4-oxy)-3-methyl-4-homopiperidino-3-butanol.
182. 2-(4'-Trifluoromethylbiphenylyl-4-oxy)-3-methyl-4-(4-methylpiperidino)-3-butanol.
183. 2-(4'-Trifluoromethylbiphenyl-4-oxy)-3-methyl-4-(2,6-dimethylpiperidino)-3-butanol.
184. 2-(4'-Trifluoromethylbiphenylyl-4-oxy)-3-methyl-4-(3,5-dimethylpiperidino)-3-butanol.
185. 2-(4'-Trifluoromethylbiphenyl-4-oxy)-2,3-dimethyl-4-piperidino-3-butanol.
186. 2-(4'-Trifluoromethylbiphenylyl-4-oxy)-2,3-dimethyl-4-morpholino-3-butanol.
187. 2-(4'-Trifluoromethylbiphenylyl-4-oxy)-2,3-dimethyl-4-pyrrolidino-3-butanol.
188. 2-(4'-Trifluoromethylbiphenylyl-4-oxy)-2,3-dimethyl-4-homopiperidino-3-butanol.
189. 2-(4'-Trifluoromethylbiphenylyl-4-oxy)-2,3-dimethyl-4-(4-methylpiperidino)-3-butanol.
190. 2-(4'-Trifluoromethylbiphenylyl-4-oxy)-2,3-dimethyl-4-(2,6-dimethylpiperidino)-3-butanol.
191. 2-(4'-Trifluoromethylbiphenylyl-4-oxy)-2,3-dimethyl-4-(3,5-dimethylpiperidino)-3-butanol.

EXAMPLE 192

A mixture of 2.26 g of 1-(biphenylyl-4-oxy)-2,3-epoxypropane, 15 ml of DMSO and 3 g of 2,6-dimethylpiperidine is heated overnight at 100°. The mixture is then poured into ice water and the 1-(biphenylyl-4-oxy)-3-(2,6-dimethylpiperidino)-2-propanol which has precipitated is filtered off and washed with water. M.p. 110°–111° (from isopropanol).

EXAMPLE 193

A mixture of 22.6 g of 1-(biphenylyl-4-oxy)-2,3-epoxypropane and 20 ml of piperidine is warmed overnight at 100°. The mixture is evaporated and the resulting 1-(biphenylyl-4-oxy)-3-(2,6-dimethylpiperidino)-2- propanol is recrystallised from isopropanol. M.p. 110°–111°.

EXAMPLE 194

A mixture of 2.63 g of 1-(biphenylyl-4-oxy)-3-chloro-2-propanol and 5 g of 2,6-dimethylpiperidine is heated for 10 hours at 100°. The mixture is evaporated and the resulting 1-(biphenylyl-4-oxy)-3-(2,6-dimethylpiperidino)-2-propanol is recrystallised from isopropanol. M.p. 110°–111°.

EXAMPLE 195

A mixture of 17 g of 4-hydroxydiphenyl, 20.55 g of 1-chloro-3-(2,6-dimethylpiperidino)-2-propanol, 8 g of sodium hydroxide, 400 ml of ethanol and 20 ml of water is heated for 10 hours at 100°. The mixture is evaporated to dryness, the residue is treated with dilute hydrochloric acid and ether, the phases are separated, the aqueous phase is rendered alkaline with concentrated sodium hydroxide solution and the resulting 1-(biphenylyl-4-oxy)-3-(2,6-dimethylpiperidino)-2-propanol is filtered off and recrystallised from isopropanol. M.p. 110°–111°.

EXAMPLE 196

A mixture of 24.3 g of 1-amino-3-(biphenylyl-4-oxy)-2-propanol, 13.8 g of potassium carbonate, 28.1 g of 2,6-dibromoheptane and 100 ml of n-butanol is boiled for 24 hours, whilst stirring. The mixture is filtered, the filtrate is evaporated and the resulting 1-(biphenylyl-4-oxy)-3-(2,6-dimethylpiperidino)-2-propanol is recrystallised from isopropanol. M.p. 110°–111°.

EXAMPLE 197

A mixture of 3.37 g of 1-(biphenylyl-4-oxy)-3-(2,6-dimethylpiperidino)-acetone [obtainable from 4-hydroxydiphenyl and 1-bromo-3-(2,6-dimethylpiperidino)-2-propanol], 400 mg of NaBH$_4$ and 300 ml of methanol is stirred for 3 hours at 25°. Water is added, the mixture is concentrated and the resulting 1-(biphenylyl-4-oxy)-3-(2,6-dimethylpiperidino)-2-propanol is filtered off. M.p. 110°–111°.

EXAMPLE 198

A Grignard solution is prepared from 0.24 g of magnesium and 1.42 g of methyl iodide in 50 ml of absolute tetrahydrofuran and this solution is then added dropwise, whilst stirring and cooling, to a solution of 3.37 g of 1-(biphenylyl-4-oxy)-3-(2,6-dimethylpiperidino-acetone in 50 ml of tetrahydrofuran. After stirring at 25° for 2 hours, the mixture is decomposed with ice and dilute hydrochloric acid, rendered alkaline with NaOH and extracted with chloroform and the extract is dried and evaporated to give 1-(biphenylyl-4-oxy)-2-methyl-3-(2,6-dimethylpiperidino)-2-propanol.

EXAMPLE 199

A mixture of 3.53 g of (1-biphenylyl-4-oxy)-3-(2,6-dimethyl-4-oxopiperidyl)-2-propanol [obtainable from 1-(biphenylyl-4-oxy)-2,3-epoxypropane and 2,6-dimethyl-4-piperidone], 1.5 g of KOH, 2.5 ml of 85% strength hydrazine and 25 ml of diethylene glycol is warmed for 1 hour at 100°. The temperature is raised slowly until the hydrazone is decomposed and the mixture is boiled for a further 4 hours, allowed to cool and worked up with water and chloroform to give 1-(biphenylyl-4-oxy)-3-(2,6-dimethylpiperidino)-2-propanol, m.p. 110°–111°.

EXAMPLE 200

A solution of 3.25 g of 2-hydroxy-3-(biphenylyl-4-oxy)-propionic acid 2,6-dimethylpiperidide [obtainable from the corresponding ethyl ester and 2,6-dimethylpiperidine] in 60 ml of THF is added dropwise, whilst stirring, to a suspension of 1 g of LiAlH$_4$ in 50 ml of absolute ether. The mixture is boiled for a further 20 hours and worked up in the customary manner to give 1-(biphenylyl-4-oxy)-3-(2,6-dimethylpiperidino)-2-propanol, m.p. 110°–111°.

The examples which follow relate to pharmaceutical preparations containing biphenylyl ethers of the general formula I:

EXAMPLE A: TABLETS

A mixture consisting of 300 g of 1-(biphenylyl-4-oxy)-3-(2,6-dimethylpiperidino)-2-propanol, 500 g of lactose, 160 g of maize starch, 20 g of cellulose powder and 20 g of magnesium stearate is pressed into tablets in the customary manner in such a way that each tablet contains 300 mg of the active compound

EXAMPLE B: DRAGÉES

Tablets are pressed analogously to Example A and are then coated in the customary manner with a coating consisting of sugar, maize starch, talc and tragacanth.

EXAMPLE C: CAPSULES 1 kg of 1-(biphenylyl-4-oxy)-3-(2,6-dimethylpiperidino)-2-propanol is filled into hard gelatine capsules in the customary manner in such a way that each capsule contains 100 mg of the active compound.

Tablets, dragées and capsules which contain one or more of the remaining active compounds of the formula I or its physiologically acceptable acid addition salts, can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound selected from the group consisting of biphenylyl ethers of the formula

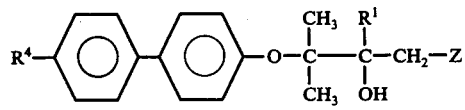

wherein R$^1$ is H or CH$_3$; R$^4$ is H, F, Cl, Br or CF$_3$; and Z is pyrrolidino, homopiperidino or piperidino which is optionally monosubstituted or polysubstituted by alkyl of 1–4 carbon atoms or by hydroxyl; and the physiologically acceptable acid addition salts thereof.

2. A compound according to claim 1, wherein R$^1$ is H.

3. A compound according to claim 1, wherein R$^4$ is H, F or Cl.

4. A compound according to claim 1, wherein R$^4$ is H.

5. A compound according to claim 1, wherein Z is pyrrolidino, homopiperidino or piperidino, each being unsubstituted or which is monosubstituted or polysubstituted by methyl or hydroxyl.

6. A compound according to claim 5, wherein Z is monosubstituted to tetrasubstituted by methyl.

7. A compound according to claim 6, wherein Z is piperidino monosubstituted or polysubstituted by methyl.

8. A compound according to claim 1, wherein $R^1$ is H and Z is piperidino, homopiperidino, 4-methylpiperidino or 2,6-dimethylpiperidino.

9. A compound according to claim 1, 2-(biphenylyl-4-oxy)-2-methyl-4-piperidino-3-butanol.

10. A compound according to claim 1, 2-(biphenylyl-4-oxy)-2-methyl-4-homopiperidino-3-butanol.

11. A compound according to claim 1, 2-(biphenylyl-4-oxy)-2-methyl-4-(4-methylpiperidino)-3-butanol.

12. A compound according to claim 1, 2-(4'-bromobiphenylyl-4-oxy)-2-methyl-4-piperidino-3-butanol.

13. A compound according to claim 1, 2-(biphenylyl-4-oxy)-2,3-dimethyl-4-piperidino-3-butanol.

14. A pharmaceutical composition comprising an elevated serum lipoprotein-lowering amount of a compound according to claim 1 in admixture with a pharmaceutically acceptable carrier.

15. A process for lowering elevated serum cholesterol and/or triglyceride levels in humans which comprises administering a safe and effective amount of a compound according to claim 1 to a living human being so afflicted for a period of time sufficient to reduce said elevated serum cholesterol and/or triglyceride levels.

* * * * *